US005699437A

United States Patent [19]

Finn

[11] Patent Number: 5,699,437

[45] Date of Patent: Dec. 16, 1997

[54] ACTIVE NOISE CONTROL SYSTEM USING PHASED-ARRAY SENSORS

[75] Inventor: Alan M. Finn, Amston, Conn.

[73] Assignee: United Technologies Corporation, Hartford, Conn.

[21] Appl. No.: 521,150

[22] Filed: Aug. 29, 1995

[51] Int. Cl.$^6$ .............................. A61F 11/06; H03B 29/00

[52] U.S. Cl. .............................. 381/71

[58] Field of Search .............................. 381/71, 94, 92; 367/901; 128/661.01

[56] References Cited

U.S. PATENT DOCUMENTS

| | | | |
|---|---|---|---|
| 4,071,848 | 1/1978 | Leeper | 343/844 |
| 4,589,137 | 5/1986 | Miller | 381/94 |
| 4,677,676 | 6/1987 | Eriksson | 381/71 |
| 4,815,139 | 3/1989 | Eriksson et al. | 381/71 |
| 4,829,590 | 5/1989 | Ghose | 455/63 |
| 5,216,721 | 6/1993 | Melton | 381/71 |
| 5,216,722 | 6/1993 | Popovich | 381/71 |
| 5,343,211 | 8/1994 | Kott | 342/379 |
| 5,438,624 | 8/1995 | Lewiner et al. . | |
| 5,515,060 | 5/1996 | Hussain et al. . | |
| 5,581,620 | 12/1996 | Brandstein et al. | 381/92 |

FOREIGN PATENT DOCUMENTS

| | | |
|---|---|---|
| 0 256 686 A1 | 2/1988 | European Pat. Off. . |
| 0 557 071 A2 | 8/1993 | European Pat. Off. . |
| 0 601 934 A1 | 6/1994 | European Pat. Off. . |
| WO 91/15896 A1 | 10/1991 | WIPO . |

OTHER PUBLICATIONS

International Search Report for PCT/US96/13306, mailed Nov. 27, 1996; for the PCT application that corresponds to United States Application 08/521,150.

Kerem, Samuel, "Dual microphones separate voice from noise." EDN–Electrical Design News, vol. 39, No. 13, Jun. 23, 1994, p. 82.

Eriksson, L. J., "Recursive Algorithms for Active Noise Control." International Symposium on Active Control of Sound and Vibration, Apr. 9–11, 1995, Tokyo, Japan, pp. 137–146.

Johnson, Don H. and Dudgeon, Dan E., "Array Signal Processing: Concepts and Techniques", pp. 77–106.

Eriksson, "Development of the filtered–U algorithm for active noise control." J. Acoust. Soc. Am. 89 (1), Jan. 1991, pp. 257–265.

Widrow et al., "Adaptive Signal Processing", Ch. 11, Adaptive Control Systems, pp. 288–297.

Takahashi et al., "Self–adapting Multiple Microphone System." Sensors and Actuators, A21–A23 (1990), pp. 610–614.

Flanagan, J. L. et al., "Computer–steered microphone arrays for sound transduction in large rooms." J. Acoust. Soc. Am., vol. 78, No. 5, Nov. 1985, pp. 1508–1518.

Flanagan, J. L. et al., "Autodirective Microphone Systems." Acustica, vol. 73 (1991), pp. 58–71.

*Primary Examiner*—Curtis Kuntz
*Assistant Examiner*—Ping W. Lee
*Attorney, Agent, or Firm*—Gerald L. DePardo

[57] ABSTRACT

An active noise control system is provided with a plurality of error sensor arrays 50,77 which provide signals on lines 64–74,90–100 to beam forming and beam steering logic 76 which cause the arrays 50,77 to exhibit acoustic response profiles 104,106, respectively. The profiles 104,106 intersect in a predefined region 116 to be quieted. The logic 76 provides signals on lines 118, one for each region to be quieted, to active noise control (ANC) logic 20 which also receives inputs from feedforward sensing microphones 10 and provides output signals to acoustic speakers 24 which generate anti-noise 26 to cancel the noise in the quiet region 116. The quiet region 116 may be selectively positioned to any region in the room by steering the beams 104,108. Alternatively, the system may have a plurality of distributed sensors which, when taken together, have an overall maximum (main lobe) acoustic response at a predetermined selectable quiet region.

11 Claims, 14 Drawing Sheets

ACTIVE NOISE CONTROL SYSTEM USING PHASED-ARRAY SENSORS

TECHNICAL FIELD

This invention relates to active noise control, and more particularly to the use of phased-array sensors in an active noise control system.

BACKGROUND ART

It is known in the art of adaptive (or active) noise (or vibration) control (ANC) systems to use one or more error sensors, e.g., microphones, to detect an undesired noise (or vibration). These error sensors provide feedback signals to an active noise control (ANC) circuit. The control circuit attempts to drive the error signal to zero by producing acoustic "anti-noise" which has the same amplitude and opposite phase of the undesired noise. The noise and anti-noise cancel each other, thereby reducing or eliminating the undesired noise. Typical multi-sensor controllers include those described in U.S. Pat. Nos. 4,815,139, entitled "Active Acoustic Attenuation System for Higher Order Mode Non-Uniform Sound Field In a Duct", to Eriksson et al; 5,216,721, entitled "Multi-channel Active Acoustic Attenuation System", to Melton; and 5,216,722, entitled "Multi-Channel Active Attenuation System with Error Signal Inputs", to Popovich.

In the prior art, the error sensors detect the undesired noise at the sensor's physical location. This requires the error sensors to be located in the space where reduced noise is desired. In some cases, it is not acceptable to have sensors near the occupants' heads (or ears), e.g., in an elevator cab. In other applications where sensors may be placed near the occupants heads, e.g., in an automobile or aircraft, there might be two error sensors in each headrest for each occupant. In that case, if there is a large number of occupants, a large number of sensors is required, making such a system quite expensive.

Some active noise control systems provide for the use of phased-array sensors, such as in U.S. Pat. No. 4,829,590 entitled "Adaptive Noise Abatement System", to Ghose. In such systems, the error sensors are configured in a phased-array to provide directional sensitivity (or directivity gain) for the sensor array receiving the noise signal. However, such a configuration is still responsive to noise at the microphone location. Thus, such sensors also detect and cancel noise at the sensor location. Further, because such systems provide directionally sensitive noise detection in a sensed region, these systems cannot quiet selective locations within the sensed region and remote from the sensors which are desired to be quieted.

Thus, it would be desirable to provide an active noise (or vibration) control system which does not have the drawbacks associated with the prior art discussed hereinbefore.

DISCLOSURE OF INVENTION

Objects of the invention include provision of an active noise control system which can detect and eliminate noise at selective locations remote from error sensing elements.

According to the present invention, an active noise control system comprises sensor means for detecting noise waves and for providing noise signals indicative of the waves; beam means for receiving the noise signals, for causing the sensor means to have an acoustic response profile which is selectively responsive to a predetermined quiet region remote from the sensor means, and for providing a beam signal indicative of noise at the quiet region; and noise control means responsive to the beam signal for providing an anti-noise signal which substantially cancels the noise at the quiet region.

According further to the present invention, the sensing means comprises a plurality of sensor arrays. According still further to the present invention, the sensing means comprises a plurality of distributed sensors.

Still further according to the present invention at least two of the sensors are spaced apart no more than one half of the wavelength of the highest frequency of the noise waves to be canceled. According further to the present invention, feedforward sensing means are provided for sensing the noise waves and for providing a feedforward noise signal to the noise control means.

This invention represents a significant improvement over the prior art by using a plurality of phased-arrays of sensors which have acoustic beams which intersect and define a volume of space to be quieted which is remote from the sensors. Alternatively, the system may have a plurality of distributed sensors which when taken together, have an overall maximum (or main lobe) acoustic response at a predetermined volume to be quieted. Thus, the sensors need not be located at the region where the noise is to be canceled (i.e., the quiet zone) and will detect only the regions of space desired to be quieted. Also, the sensor arrays may sense multiple locations simultaneously or sequentially using acoustic beam steering techniques. As a result, the invention may use a lower total number of sensors than the number of regions to be quieted. Further, sensor arrays may be mounted at convenient locations in the walls, ceiling, and/or floor of an enclosure to facilitate the detection and cancellation of noise at a location remote from the sensors. Still further, the sensors need not be oriented in any particular geographic layout, and thus may be placed where convenient and/or where maximum quieting in the desired regions occurs. Typical applications include a room, elevator, automobile, or aircraft cabin; however, the invention will work for any active noise cancellation application.

The foregoing and other objects, features and advantages of the present invention will become more apparent in light of the following detailed description of exemplary embodiments thereof as illustrated in the accompanying drawings.

BEST MODE FOR CARRYING OUT THE INVENTION

Figure 1:
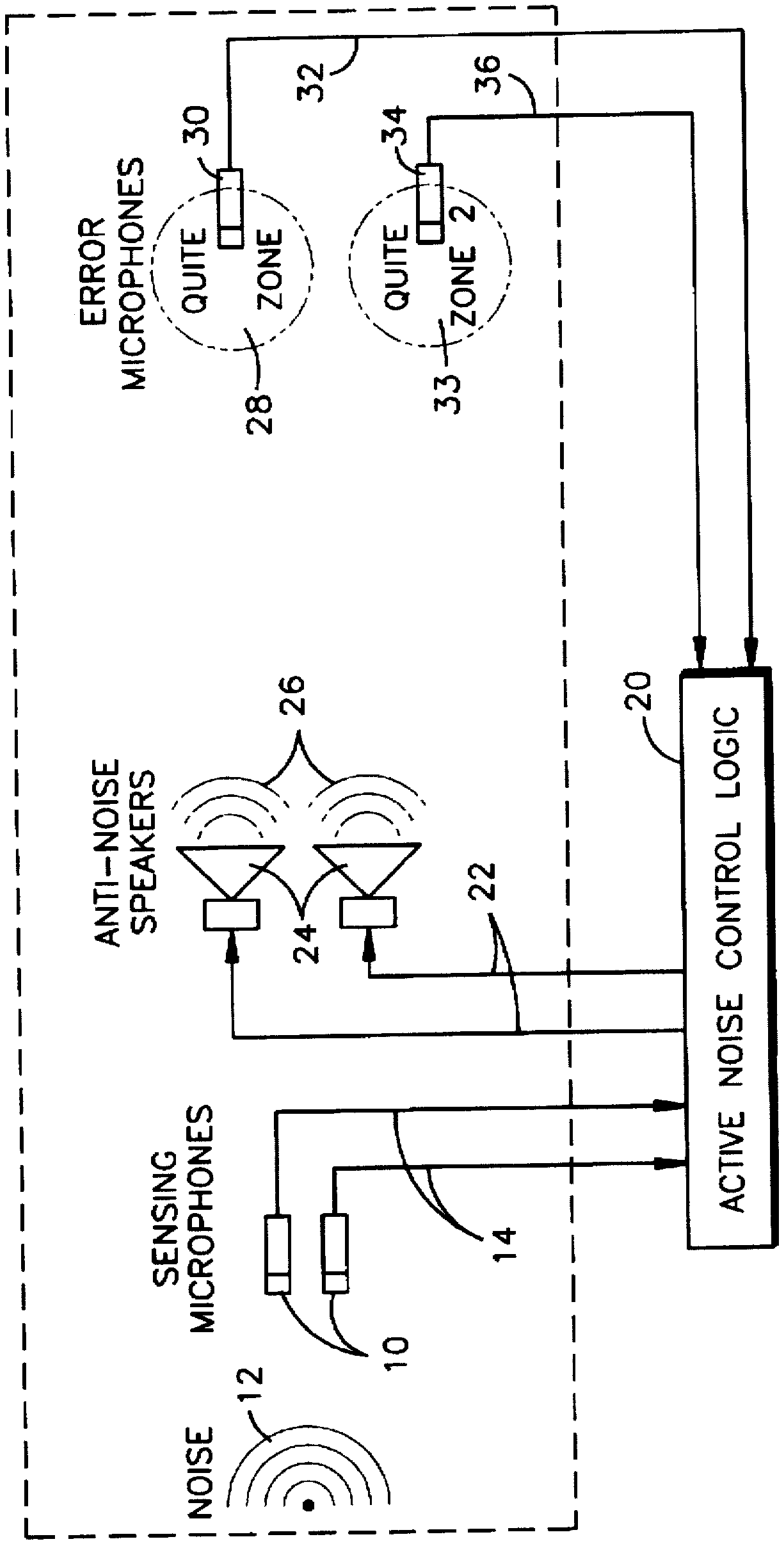
FIG. 1 PRIOR ART
FIG. 1 is a functional block diagram of a prior art active noise control system.

Referring to FIG. 1, a prior art active noise control system comprises sensing microphones 10 which sense noise 12 and provide electrical signals on lines 14 to active noise control (ANC) logic 20. The active noise control logic 20 provides electrical signals on lines 22 to acoustic "anti-noise" speakers 24. As used herein the term "noise" is used to mean any type of acoustic waves including sound and/or vibration. The anti-noise speakers 24 generate acoustic noise 26 which is equal in magnitude and opposite in phase to the noise 12 so as to cancel the noise in a "quiet zone" 28. An error microphone 30, e.g., an omni-directional microphone, senses noise in the quiet zone 28 and provides an electrical signal on a line 32 to the active noise control logic 20 to adjust the output signals 26 of the speakers 24 so as to cause the noise in the quiet zone 28 to be substantially reduced or zero. Thus, the sensing microphones 10 can be viewed as a feed-forward reference (or compensation) for the control logic 20, and the error microphone 30 can be viewed as a trim control to drive the noise in the quiet zone 28 to zero, as is known.

However, if it is desired for the quiet zone 28 to be located away from the error microphone 30 (e.g., because it is inconvenient or impractical to place the error microphone at the quiet zone), then the prior art configuration of quieting the region 28 at the error microphone 30 is not acceptable. Also, if a second quiet zone 33 is desired to be quieted, another sensor 34 is needed. The sensor 34 provides a second error signal on a line 36 to the active noise control logic 20. Thus, for such a system the number of error microphones is equal to or greater than the number of locations to be quieted (or quiet zones).

Figure 2:
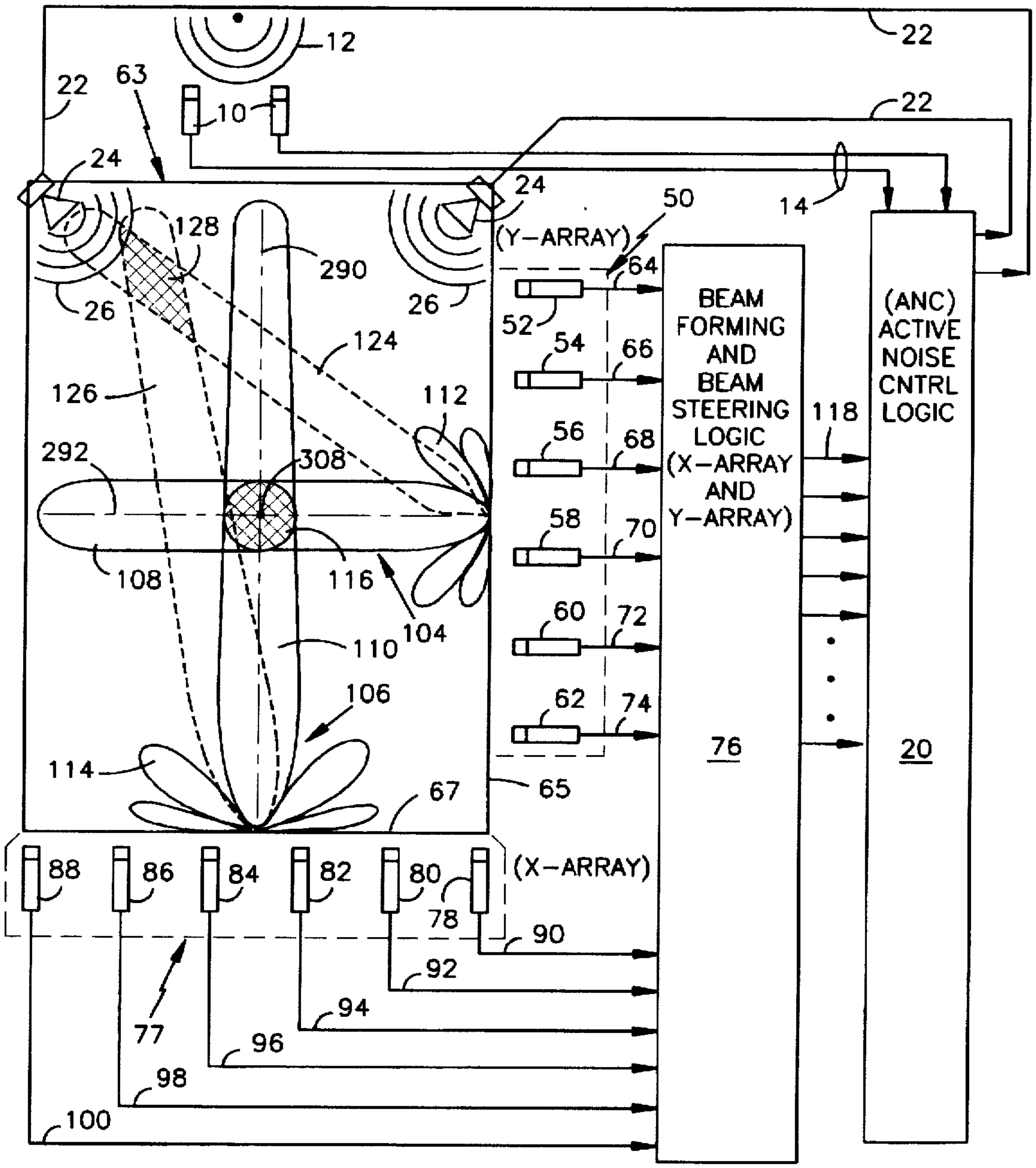
FIG. 2 is a top view of a room and a functional block diagram of an active noise control system employing two phased-arrays of sensors, in accordance with the present invention.

Referring now to FIG. 2, an active noise control system of the present invention comprises a first phased-array (y-array) of error microphones 50 comprising a plurality of (e.g., six) error microphones 52–62 mounted along one wall 65 in a room 63. The microphones 52–62 provide electrical signals on lines 64–74 indicative of the acoustic response of the microphones 52–62, respectively. The electrical signals 64–74 are fed to beam forming and beam steering logic 76 (discussed hereinafter). Similarly, a second phased-array (x-array) of error microphones 77 comprises a plurality of (e.g., six) microphones 78–88 and is mounted along a wall 67 perpendicular to the wall 65 in the room 63. Each of the microphones 78–88 provides electrical signals on lines 90–100 indicative of the acoustic response from the microphones 78–88, respectively. The lines 90–100 are also fed to the beam forming and beam steering logic 76. Other numbers of microphones in the arrays 50,77 may be used if desired. Also, instead of microphones, any sensors capable of detecting acoustic noise waves and of providing signals indicative thereof may be used if desired.

The beam forming and beam steering logic 76 creates acoustic response profiles 104,106 (shown as polar-coordinate plots) associated with the y-array 50 and x-array 77 of sensors, respectively. Each of the response profiles have a directionally sensitive response region or main beam (or main lobe) 108,110, respectively, and side lobes 112,114, respectively, for the profiles 104,106, respectively. The side lobes 112,114 have lower response characteristics than the main beams 108,110. This indicates that when sound waves propagate toward the arrays 50,77 from a direction different from where the main beams 108,110 are positioned, the microphone arrays 50,77, respectively, will have a much lower acoustic response than if the waves were propagating in a direction along the main beams 108,110.

The beam forming and beam steering logic 76 provides output signals on lines 118 to the active noise control logic 20. The number of signals 118 represent the number of regions or quiet zones to be sensed by the multiple microphone array system.

The active noise control logic 20 may be the same as the prior art active noise control logic described hereinbefore with FIG. 1, e.g., a standard "Filtered X" or "Filtered-U" controller having the desired bandwidth response, such as the controllers described in Eriksson, L. J., "Development of the Filtered-U Algorithm for Active Noise Control", Journal of the Acoustic Society of America, Vol. 89, No. 1 (January 1991), pp. 257–265; U.S. Pat. No. 4,677,676, entitled "Active Attenuation System with On-line Modeling of Speaker Error Path and Feedback Path" to Eriksson et al, or in the text book Widrow et al, "Adaptive Signal Processing", Prentice Hall, 1985, pp 288–297, or any corresponding multi-channel ANC controllers such as those described in U.S. Pat. Nos. 4,815,139, entitled "Active Acoustic Attenuation System for Higher Order Mode Non-Uniform Sound Field In a Duct", to Eriksson et al; 5,216,721, entitled "Multi-channel Active Acoustic Attenuation System", to Melton; and 5,216,722, entitled "Multi-Channel Active Attenuation System with Error Signal Inputs", to Popovich, all of which are hereby incorporated by reference. However, the active noise control logic 20 may be any form of active noise control logic which receives inputs indicative of the acoustic noise to be quieted and provides output anti-noise signals.

The beam forming and steering logic 76 (and for any other beam form and beam steer logic discussed hereinafter) and the ANC logic 20 may likely be performed by a programmed digital computer having sufficient memory and processing capability to perform the functions described herein. Alternatively, all or a portion of the logics 76 and/or 20 may be performed by digital and/or analog circuitry configured so as to perform the functions described herein.

The active noise control logic 20 also receives input signals from the sensing microphones 10 on the lines 14 as discussed hereinbefore with FIG. 1 and provides output signals on the lines 22 to the anti-noise speakers 24 which provide anti-noise 26. More or less speakers 24 may be used if desired. Also, the placement of the speakers 24 may be in other locations to optimize the cancellation effects, as is known, and more or less speakers may be used if desired. Further, instead of speakers, any output transducer capable of producing anti-noise (acoustic and/or vibration) waves in response to drive signals from the ANC logic 20 may be used if desired.

The two acoustic beams 108,110 of the microphone arrays 50,77, respectively, intersect in a quiet zone region 116 where the acoustic response of the combined X and Y arrays is a maximum. Accordingly, each of the lines 118 from the beam forming logic 76 represents a signal indicative of acoustic noise at the quiet region 116. Thus, the invention provides for detection and cancellation of noise at a quiet zone (e.g., the region 116) which is located remote from the microphones 52–62 and 78–88.

Also, the beam forming and beam steering logic 76 may alter the direction of the main beams 108,110 to detect other regions in the room 63. For example, if the main beam 108 from the array 50 is rotated clockwise, as indicated by a main beam 124, and the main beam 110 from the array 77 is rotated counterclockwise, as indicated by a beam 126, they will intersect in a region 128 different from the region 116.

Figure 3:
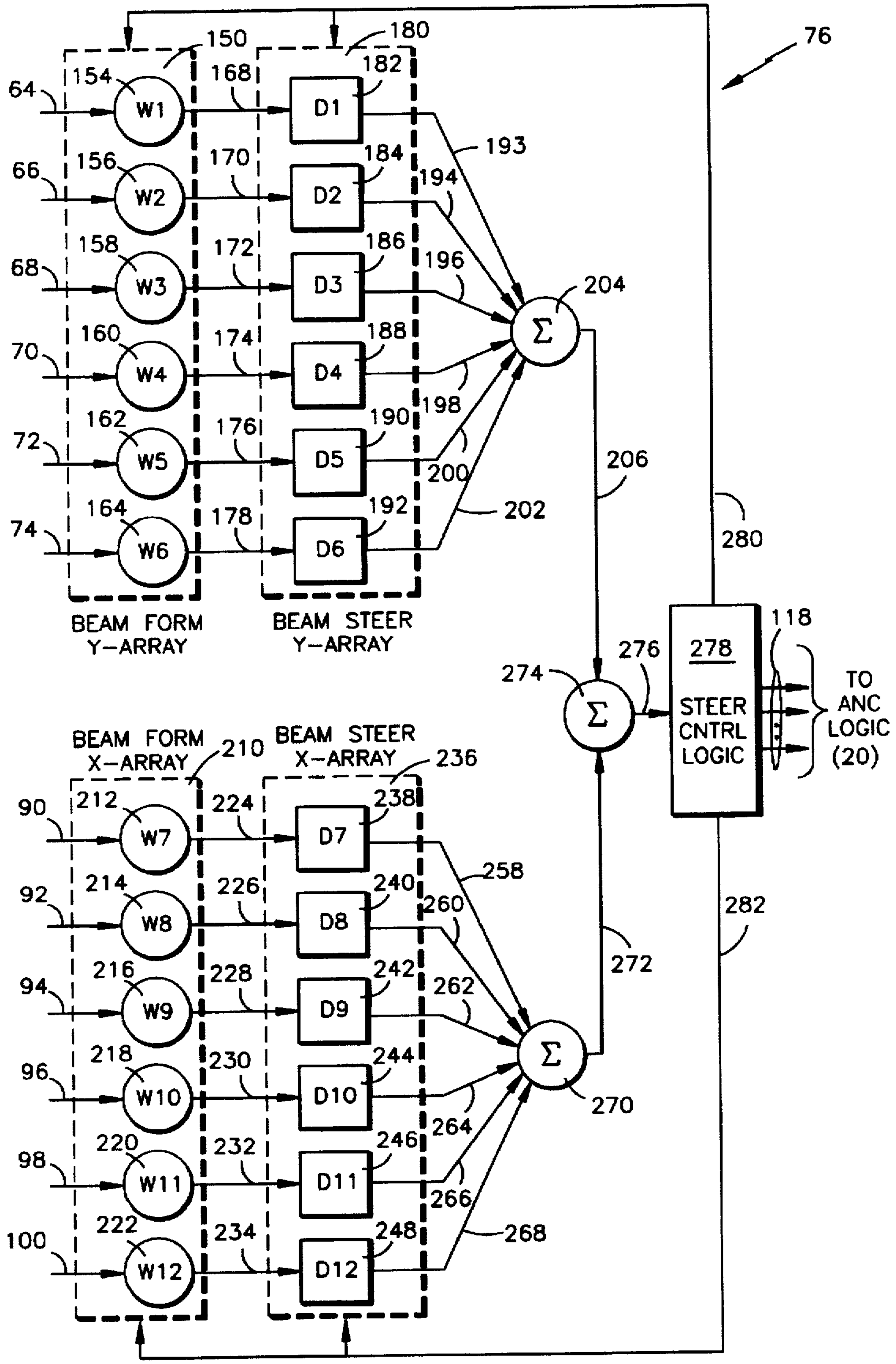
FIG. 3 is a block diagram of beam forming and beam steering logic for the system of FIG. 2, in accordance with the present invention.

Referring now to FIG. 3, as is known, microphone array directional beam forming is created by multiplying the output signals from microphones in a microphone array by a predetermined set of weighting factors (Wn). The weighting factors (Wn) multiply the signal from the associated microphone by a number which causes each of the signals from the microphone array to be a maximum when sound at a predetermined frequency is propagated from a predefined region or point in space. The weighting factors are selected so as to provide the desired acoustic response patterns 104,106 (FIG. 2) comprising the desired main lobe 108,110 and side lobes 112,114 for the y-array and x-array, respectively.

More specifically, y-array beam form logic 150 comprises six multipliers, 154–164 which multiply the signals on the lines 64–74 by weighting factors W1–W6. The beam form logic 150 provides six weighted output signals on lines 168–178 from the multipliers 154–164, respectively, to variable beam steer logic 180. The beam steer logic 180 comprises six variable delays 182–192 (D1–D6). The variable delays D1–D6 (Dn) delay (or phase shift) the input signals on the lines 168–178 by a predetermined amount of time (or degrees or radians) unique for each microphone in the y-array. By adjusting the delay (or phase shift) on the signals from each of the microphones, the central beam 108 may be turned so as to sense noise from different directions, as is known. The delays Dn may be implemented using any desired signal delay technique, such as multiplication by a complex number ($e^{j\theta}$) having a phase shift ($\theta$) associated therewith, a digital time delay (e.g., delaying the input signal by a predetermined number of sample times), or equivalent analog delay logic.

The beam steer logic 180 provides weighted delayed signals on lines 193–202 for each of the microphones 52–62, respectively. The weighted delayed signals are fed to a summer 204 which provides a sum of the signals on the lines 192–202 on a line 206 for the y-array.

A symmetrical configuration exists for the x-array comprising beam form logic 210 which comprises six multipliers 212–222 which multiply the signals on the lines 90–100 by the weighting factors w7–w12. The beam form logic 210 provides six weighted output signals on lines 224–234. The weighted signals on the lines 224–234 are fed to variable beam steer logic 236 comprising six variable delays 238–248 (D7–D12) which provides delayed signals on lines 258–268 to a summer 270. The summer 270 provides a sum of the signals on the lines 258–268 on a line 272 for the x-array.

The signals on the lines 206 and 272 are combined at a summer 274 which provides a combined x-array/y-array signal on a line 276. The signal on the line 276 is fed to steer control logic 278 which provides signals on lines 280,282 to the beam steer logics 180,236, respectively, to adjust the delays D1–D12 which redirects the beams 108,110 so as to intersect in different regions around the room 63 (FIG. 3). In certain cases, the weighting factors W1–W12 may also need to be adjusted to retain optimized acoustic response at the desired location, as indicated by the lines 280,282 also being fed to the logics 150,210, respectively. This may likely be necessary when near field analysis (discussed hereinafter) is performed to determine the weighting factors Wn. A sequential signal from each of the regions to be quieted is coupled from the line 276 to an associated one of the lines 118 which are fed to the active noise control logic 20 (FIG. 2) which adjusts the output signal 26 from the speakers 24 so as to cancel the sound in the regions sensed.

Figure 4:
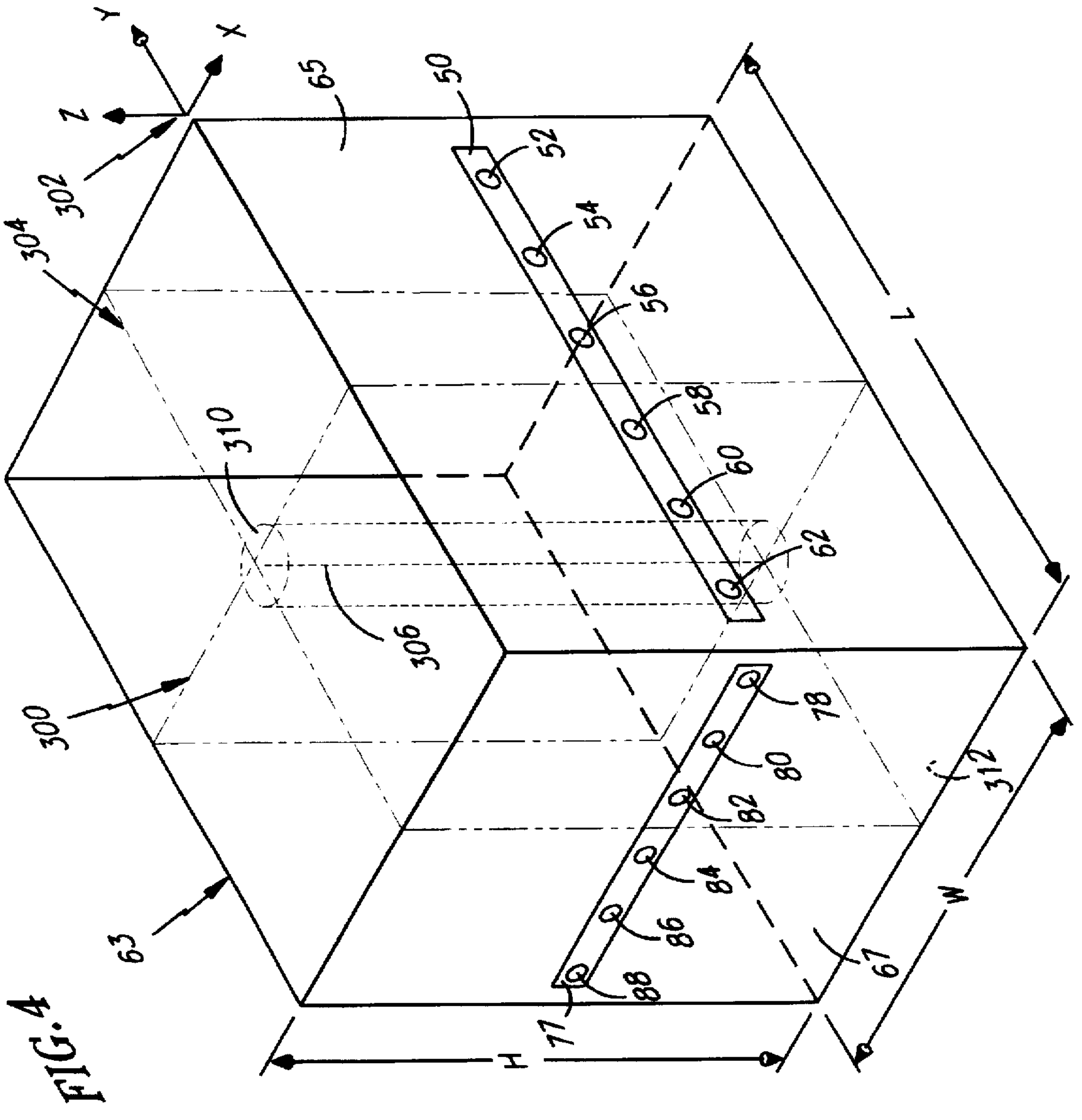
FIG. 4 is a perspective view of a room having two sensor arrays in accordance with the present invention.

Referring now to FIG. 4, the room 63 has a height "H", width "W", and length "L" of 2.5, 2.0, and 3.0 meters, respectively, and the X and Y-arrays 50,77, respectively, are placed substantially at the centers of the walls 65,67 in the room 63. When the beams 108,110 are pointed toward the center of the room 63, a central line 292 (FIG. 2) of the beam 108, for the microphone array 50, may be viewed in three dimensions as a plane 300 defined by the x-axis and the z-axis of a coordinate axis system 302. Similarly, a central line 290 (FIG. 2) of the main beam 110 for the microphone array 77 may be viewed as a plane 304 defined by the y-axis and z-axis of the coordinate system 302. The planes 300,304 intersect at a line 306 which extends the height (H) of the room 63, and, in two dimensions, appears as a point 308 (FIG. 2). Accordingly, the region 116 (FIG. 2), viewed in three dimensions, would be a column 310, extending the height (H) of the room 63.

Figure 5:
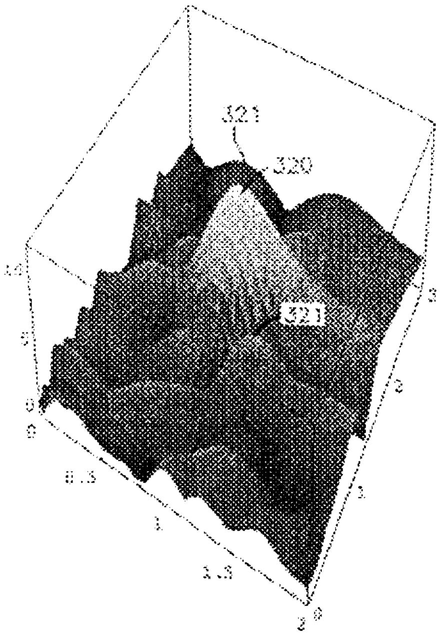
FIG. 5 is a three dimensional graph of the acoustic response of two sensor-arrays, in accordance with the present invention.
Figure 6:
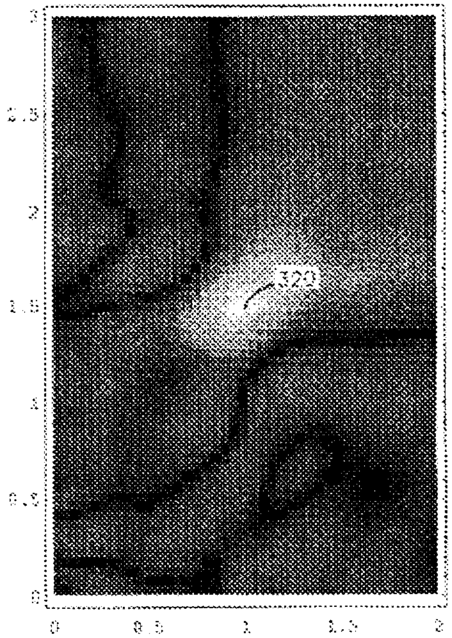
FIG. 6 is a two dimensional graph of the acoustic response of FIG. 5, in accordance with the present invention.

Referring now to FIGS. 5 and 6, if the beams 108,110 (FIG. 2) are steered to define the quiet region 116 near the center of the room 63, and the acoustic response of the arrays 50,77 are examined in the x-y plane at a height of 1.5 meters (i.e., z=1.5 meters) from the floor 312 (FIG. 4), a peak (or main lobe) microphone array response exists at a point 320 (X=1.0 m, Y=1.5 m, Z=1.5 m) in the region 116 which, in three dimensions, would be the column 310 (FIG. 4).

In that case, for a noise frequency of 450 hertz, the values for the weighting factors W1–W12 are: W1=−0.02172; W2=0.794966; W3=2.005067;W4=1.92274; W5=0.545887; W6=0.659506; W7=2.533764; W8=0.066601; W9=1.110299; W10=1.506019; W11=0.25961; and W12=0.617259, and the delays D1–D12 have the values: D1=0.00000000λ, D2=0.30200475λ, D3=0.47851537λ, D4=0.47851537λ, D5=0.30200475λ, D6=0.00000000λ, D7=0.48486530λ, D8=0.71125886λ, D9=0.83417616λ, D10=0.83417616λ, D11=0.71125886λ, D12=0.48486530λ. The delays are expressed as a fraction of the wavelength λ and normalized to the delay D1, where λ is the wavelength (in meters) of noise having a frequency f=450 Hz and the speed of sound v=345 m/sec in free space, and λ=v/f. Alternatively, the delays may be expressed as a pure time delay in seconds. The delays D1–D6 and D7–D12 within the individual sensor arrays 50,77, are symmetric since the arrays 50,77 and main beams 108,110 are centered with respect to the walls 65,67.

Thus, in that case, the response peak (or main lobe) 320 will be exhibited at the region 116 (FIG. 2) or the column 310 (FIG. 4) at the center of the room, while areas outside the center of the room have side lobes 321 with much lower microphone array response.

Figure 7:
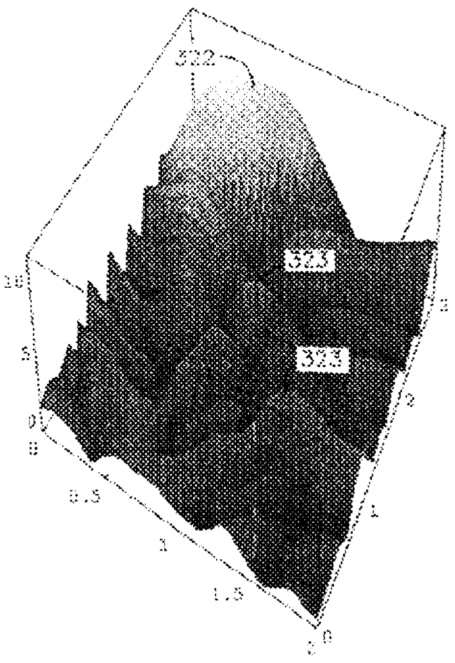
FIG. 7 is a three dimensional graph of the acoustic response of two sensor-arrays, intersecting near a corner of a room, in accordance with the present invention.
Figure 8:
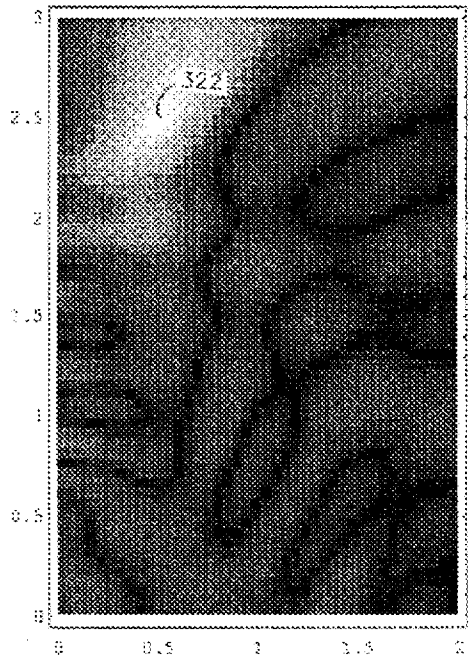
FIG. 8 is a two dimensional graph of acoustic response of FIG. 7, in accordance with the present invention.

Referring to FIGS. 7 and 8, if the beams 108,110 are steered as indicated by the beams 124,126 (FIG. 2) to define the quiet region 128 near the corner of the room 63, a peak (or main lobe) microphone array response exists at a point 322 (X=0.5 m, Y=2.5 m, Z=1.5 m) in the region 128 (FIG. 2) which, in three dimensions, would be a column (not shown) and the areas outside the region 128 have side lobes 323 with much lower acoustic response. In that case, for a noise frequency of 450 hertz, the values for the weights W1–W12 are: W1=−0.15351; W2=0.926312; W3=1.273882; W4=2.187788; W5=1.961656; W6=2.090639; W7=0.568895; W8=0.339295; W9=0.442442; W10=0.972535; W11=0.771841; and W12=0.618227, and the values for the delays D1–D12 are: D1=0.0000λ; D2=0.4809λ; D3=0.9507λ; D4=0.3965λ; D5=0.7804λ; D6=0.9819λ; D7=0.3211λ; D8=0.3740λ; D9=0.3507λ; D10=0.2529λ; D11=0.0867λ; D12=0.8612λ. The delays D1–D12 are expressed as a fraction of the wavelength λ and normalized to the delay D1, where λ is the wavelength (in meters) of noise having a frequency f=450 Hz and the speed of sound v=345 m/sec in free space, and λ=v/f. Alternatively, the delays may be expressed as a pure time delay in seconds. Also, the microphones in each array are equally spaced at λ/2. The microphones may be spaced closer if desired, but, if they are all equally spaced, they should not be spaced much farther apart than λ/2 to avoid spatial aliasing, as is known. The spacing between the arrays 50,77 is determined by the size of the room 63 and of the walls 65,67. Other microphone spacings may be used as discussed hereinafter.

The values for the weights W1–W12 and delays D1–D12 for FIGS. 5–8 were chosen by maximizing the response for the main beam (or lobe) while ensuring the side lobes were at least a 2:1 reduction from the main beam, for all twelve microphones taken as a group, at a single frequency of 450 hertz using a "near field" analysis. In particular, for the values provided herein, the optimization was performed on the software tool MATLAB® by The Math Works, Inc. of Natick, Mass., using the routine "CONSTR" in the Optimization Toolbox of FLATLAB®, which performs constrained optimization (i.e., maximize main lobe while placing a maximum allowable limit on side lobes). Also, the vertical axes of FIGS. 5 and 7 are scaled for the maximum response of one (1.0) from each sensor, giving a total maximum response of 12.

Alternatively, the type of analysis to use (i.e., far or near field) depends on the distance between the noise source and the microphones. As is known, if the noise source is close to the microphones, e.g., less than about 10–20 wavelengths, the shape of the noise waves reaching the microphones is curved and a known "near field" acoustic analysis should be used which considers the curvature of the noise waves across the microphones to maximize array accuracy. However, if the noise source is far from the microphones, e.g., greater than 10–20 wavelengths, the shape of the noise waves reaching the microphones is substantially flat and a known "far field" analysis may be used which considers the noise as plane (flat) waves. If a far field analysis is performed on the system of FIG. 2, all the delays D1–D12 would be 1 when focusing the main beams at the center of the room 63.

Figure 9:
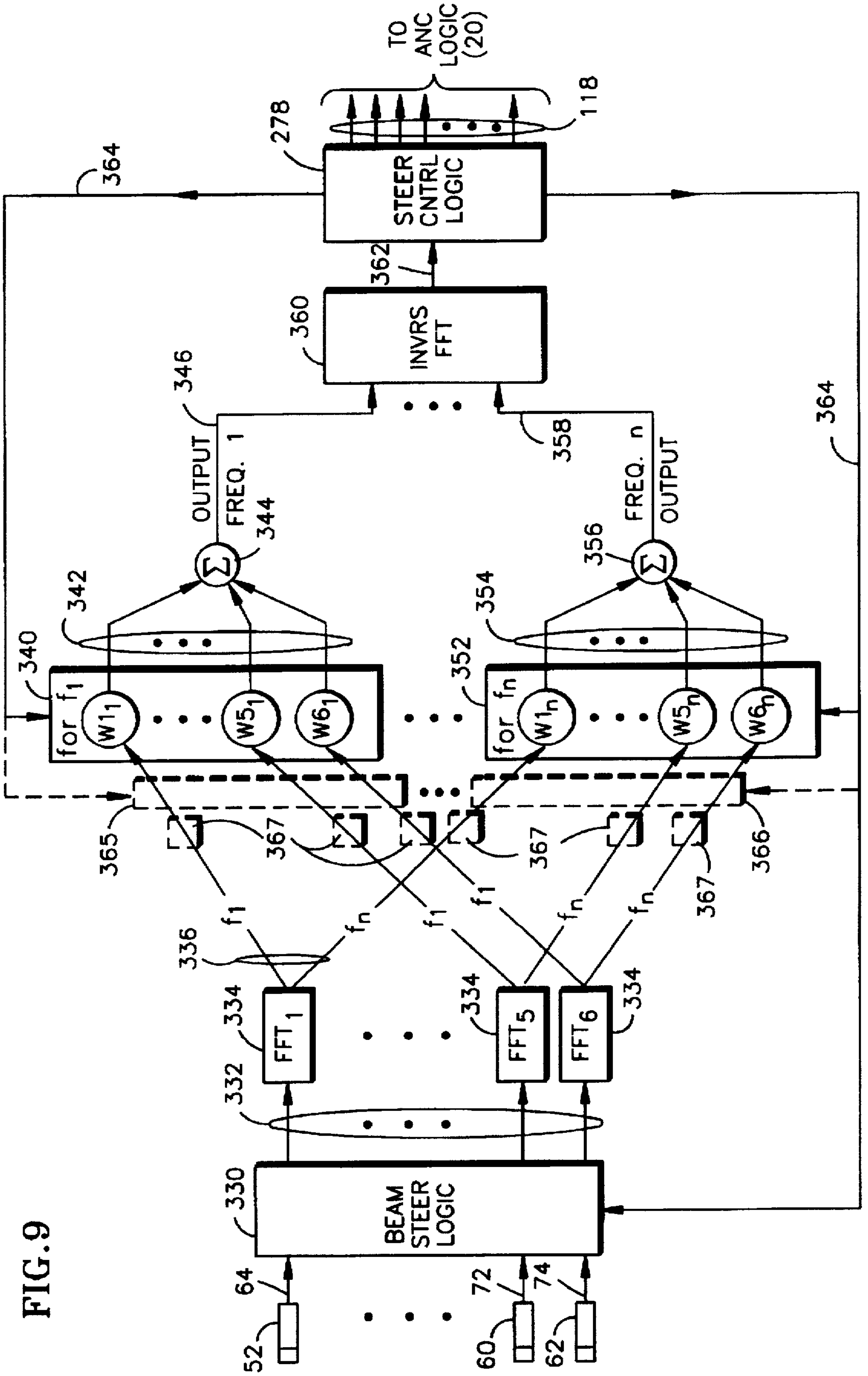
FIG. 9 is a block diagram of beam forming and beam steering logic for a broadband of frequencies, in accordance with the present invention.

Referring now to FIG. 9, because some active noise control systems quiet a broad range of frequencies, e.g., 200–800 Hz, as opposed to a single frequency, the beam forming and beam steering logic 76 described in FIG. 2 may need to be designed to provide an acoustic response which senses a plurality of frequencies. One way to obtain such broadband sensor array response is shown in FIG. 9. In particular, the microphone array 50 having the microphones 52–62 provides signals on the lines 64–74 to beam steer logic 330. The logic 330 provides a plurality of delayed signals, one for each input microphone, the same as or similar to the beam steer logics 180,236 discussed hereinbefore. Each delayed signal from each microphone is fed into Fast Fourier Transform (FFT) logics 334 on lines 332. Thus, for six microphones there would be six FFT logics 334 ($FFT_1$–$FFT_6$). Each FFT Logic 334 produces a plurality of output signals 336, one for each of the frequencies in the broadband response ($f_1$–$f_n$). The output signal from each of the FFT logics 334 corresponding to a first frequency $f_1$ are fed to a first beam forming logic 340 for the frequency $f_1$ comprising six weighting factors $W1_1$–$W6_1$ tailored for the desired acoustic response at the frequency $f_1$ similar to those of the beam forming logic 150 discussed hereinbefore with FIG. 3. The beam forming logic 340 provides six signals on lines 342 to a summer 344 which combines the signals on the lines 342 and provides a summed output signal on a line 346. Similarly, the frequency $f_n$ from each of the FFT logics 334 is fed to beam forming logic 352 which provides output signals on lines 354 indicative of the input signals multiplied by the weighting factors $W1_n$–$W6_n$ tailored for the desired acoustic response at the frequency of $f_n$. The signals on the lines 354 are fed to a summer 356 which sums the signals on the lines 354 and provides a summed output signal on a line 358.

The output frequency domain signals for each of the frequencies $f_1$–$f_n$ on the lines 346,358 are fed to inverse FFT logic 360 which converts the frequency domain signals from each of the beam forming logics 340,352 to a combined time domain signal on a line 362.

The combined sequential signal on the line 362 from each of the regions to be quieted is fed to the steer control logic 278 discussed hereinbefore with FIG. 3. The steer control logic 278 couples the sequential signal from the line 362, associated with each of the regions to be quieted, to an associated one of the lines 118 which are fed to the active noise control logic 20. The steer control logic 278 also provides an output signal on lines 364 which sets the delay times in the beam steer logic 330 for each of the successive locations to be quieted, as discussed hereinbefore. As discussed hereinbefore, in certain cases, the weighting factors Wn for the logics 340,352 may also need to be adjusted to retain optimized acoustic response at the desired location, e.g., when near field analysis is used to determine the weighting factors Wn, as indicated by the lines 364 also being fed to the logics 340,352.

The beam steer logic 330 may be placed anywhere in the path of the signal flow. In particular, when working in the far field, placing it in front of the FFTs 334 requires only six variable delays (when six error microphones are used). However, when working in the near field, the beam steer logic 330 should be placed after the FFTs 334 because there are different wave front curvatures for each different frequency, thereby allowing for unique beam steer logics 365–366 for each of the frequencies $f_1$–$f_n$. The logics 365–366 may be placed before or after the weighting logics 340,352. Also, it should be understood that because the input signals from the microphones 52–62 are converted into the frequency domain by the FFTs 334, the weighting factors Wn and the delays in the beam steer logics 365–366 (placed after the FFTs 334) will be convolution operations instead of multiplication operations, as is readily understood by those skilled in the art.

Alternatively, the inverse FFT logic 360 need not be employed and, in that case, the active noise control circuit 20 would be frequency-based instead of time-based. Further, instead of placing the inverse FFT 360 after the summers 344,356, inverse FFTs 367 may be placed before the weighting factors 340,352 and delays 365–366 and after the FFTs 334 for each frequency. In that case, the weighting factors Wn and the delays in the beam steer logics 365–366 may be multiplication operations, but many more inverse FFTs 367 would be required. Further, the microphones in the arrays for such a broadband system may be equally spaced at λ/2, where λ corresponds to the highest frequency the system must detect and cancel. The microphones may be spaced closer if desired, but, if they are all equally spaced, they should not be spaced much farther apart than λ/2 to avoid spatial aliasing, as discussed hereinbefore. Other microphone spacings may be used as discussed hereinafter.

Figure 10:
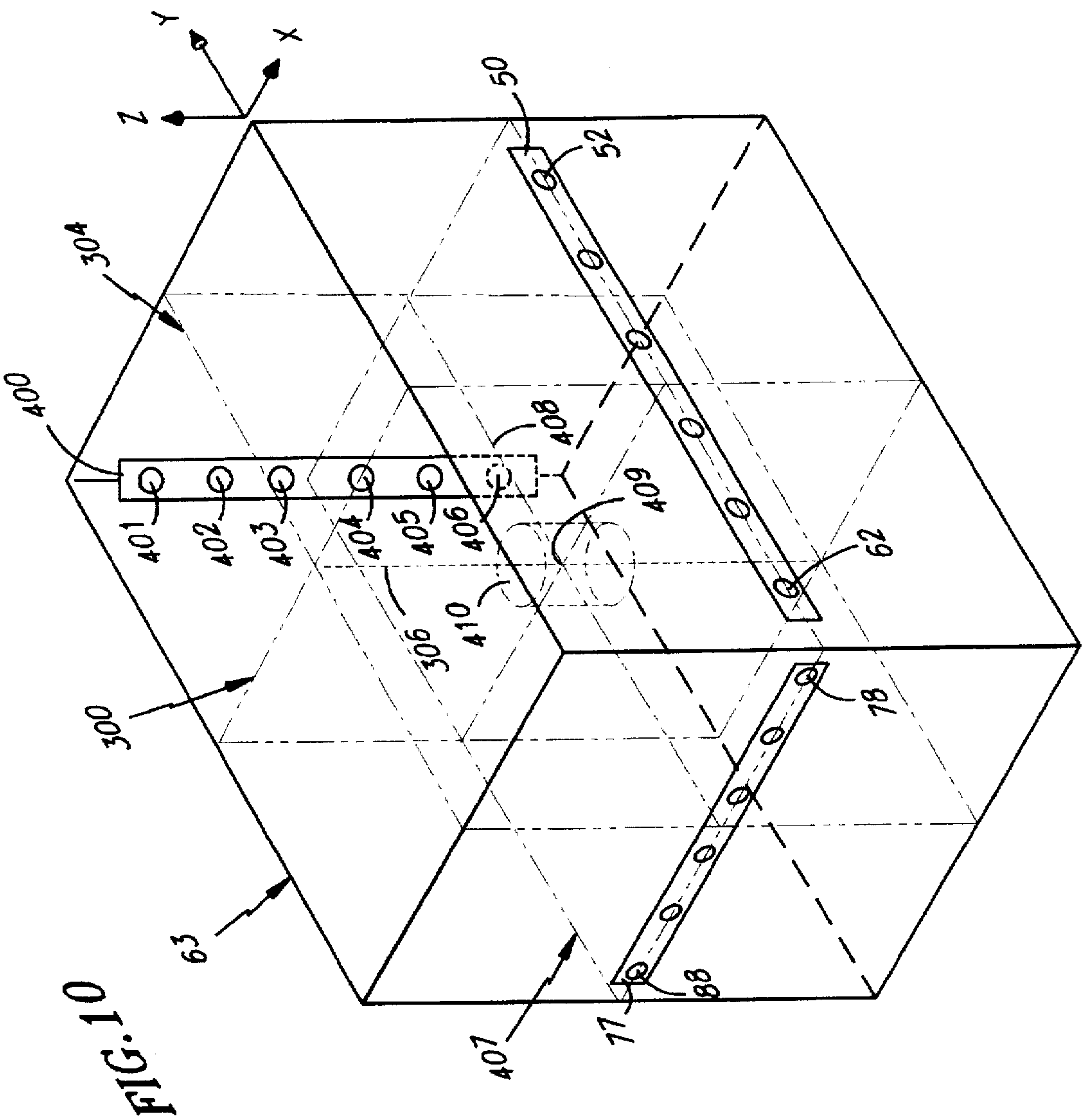
FIG. 10 is a perspective view of a room having three sensor-arrays in accordance with the present invention.

Referring now to FIG. 10, a third microphone array 400 may be placed along the height (H) or Z-axis of the room 63 comprising six microphones 401–406. The array 400 provides a third response plane 407 which intersects with the plane 304 at a line 408. All three planes 300,304,407 intersect at a point 409, and, more particularly, at a region or volume 410, when all three arrays 50,77,400 are focused to the center of the room.

Figure 11:
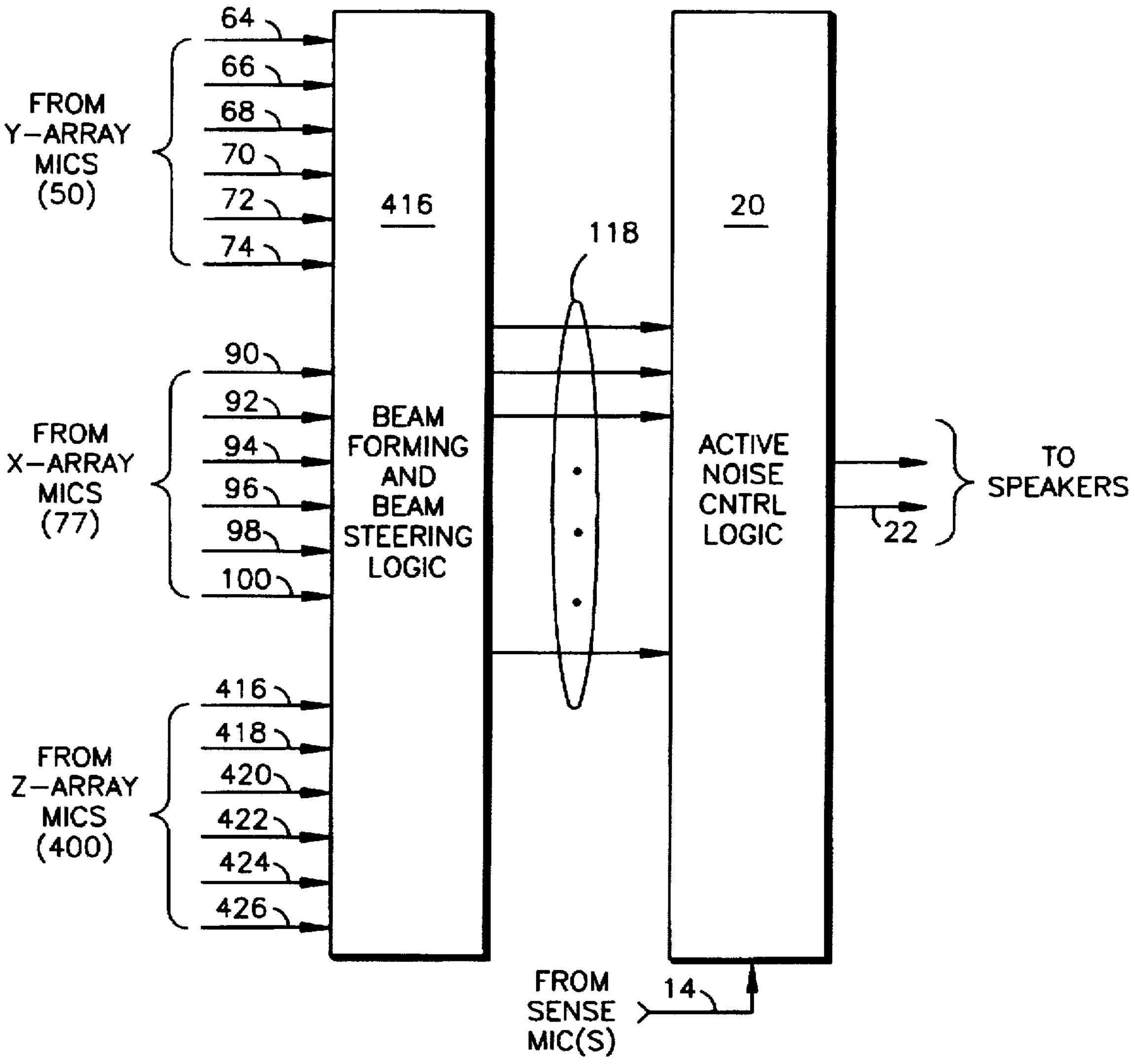
FIG. 11 is a block diagram of an active noise control system employing three phased-arrays of sensors, in accordance with the present inventions.

Referring now to FIG. 11, in the case of three sensor-arrays, signals from the y-array 50 microphones (mics) on the lines 64–74, the x-array 77 mics on the lines 90–100, and the z-array 400 mics on lines 416–426, respectively, are all fed to beam forming and beam steering logic 416 which provides the output signals 118 to the active noise control logic 20. The beam forming and beam steering logic 416 may be the same as that described hereinbefore with respect to FIG. 2, except an additional array of microphones is added to create an additional acoustic beam. This additional beam further reduces the volume which is being sensed by the microphone arrays, and hence, being quieted by the speakers 24 (FIG. 2) which are driven by the active noise control logic 20.

Figure 12:
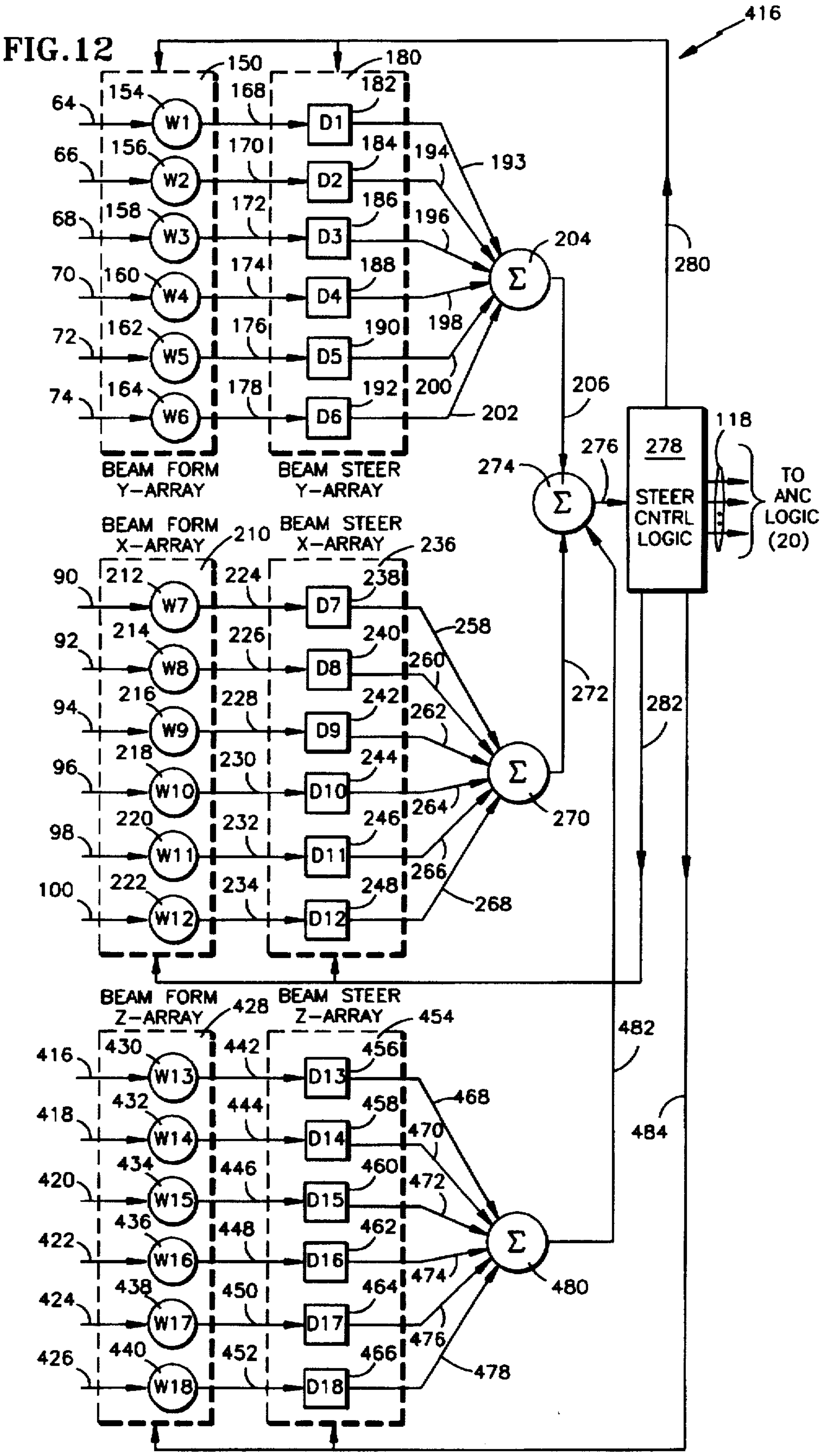
FIG. 12 is a block diagram of beam forming and beam steering logic for the system of FIG. 11, in accordance with the present invention.

Referring now to FIG. 12, in particular, signals from the microphones 401–406 (FIG. 10) on the lines 416–426 (FIGS. 11,12) are fed to z-array beam form logic 428 similar to the beam form array logics 150,210 for the y and x-arrays, respectively. The logic 428 comprises six multipliers 430–440 which multiply the signals on the lines 416–426 by weighting factors W13–W18, respectively. The beam form logic 428 provides weighted signals on lines 442–452 to variable z-array beam steer logic 454 comprising six delays 456–466, each having its own independent variable delay D13–D18. The beam steer logic 454 provides delayed weighted output signals on lines 468–478 to a summer 480 which combines the signals on the lines 468–478 onto a line 482. The line 482 is fed to the summer 274 which combines the signals on the lines 206,272, and 482 onto the line 276 to the steer control logic 278. The steer control logic 278 provides the output signals 280,282 (as discussed hereinbefore) as well as a third output signal on a line 484 to the z-array beam steer logic 454 which adjusts the delays D13–D18 to steer the acoustic response beam created by the microphone array 400. As discussed hereinbefore, in certain cases, the weighting factors W13–W18 may also need to be adjusted by the steer control logic 78 to retain optimized acoustic response at the desired location, as indicated by the lines 484 also being fed to the logic 428. The resultant output signal is provided on the lines 118 to the active noise control logic 20, one line for each volume to be quieted.

Figure 13:
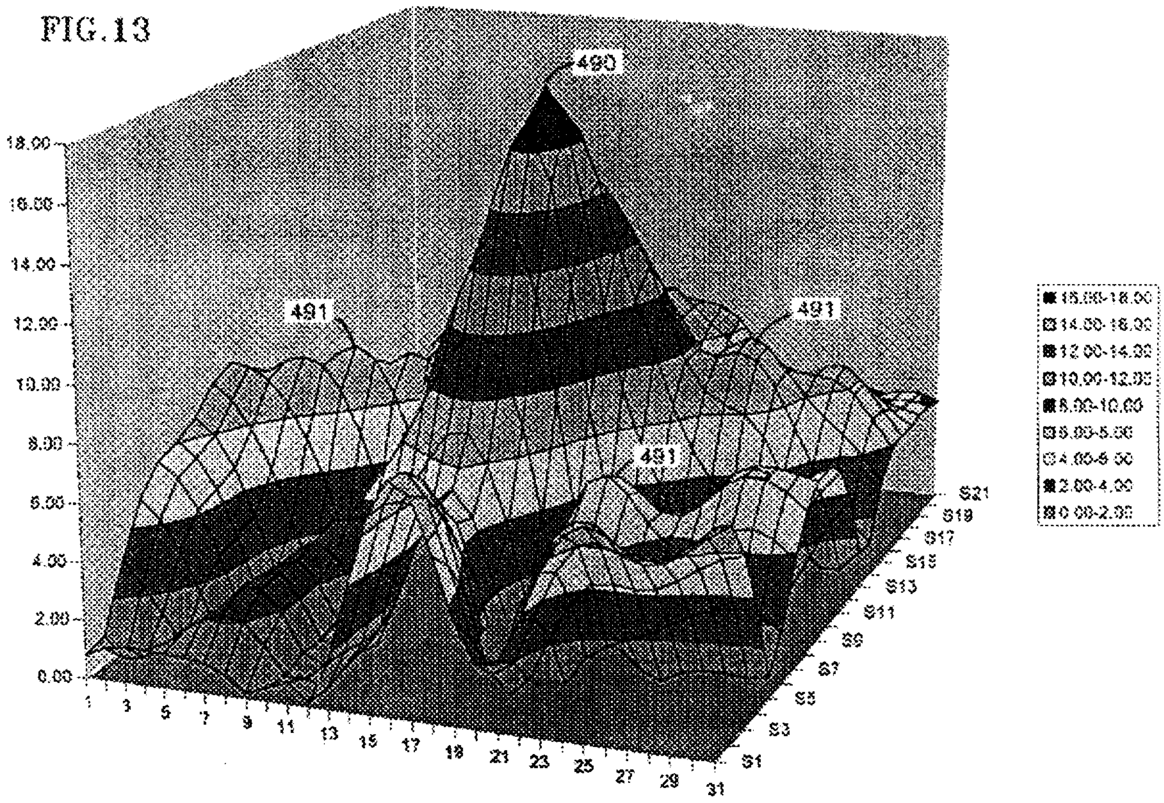
FIG. 13 is a three dimensional graph of acoustic response of three sensor-arrays at a specified height, in accordance with the present invention.
Figure 14:
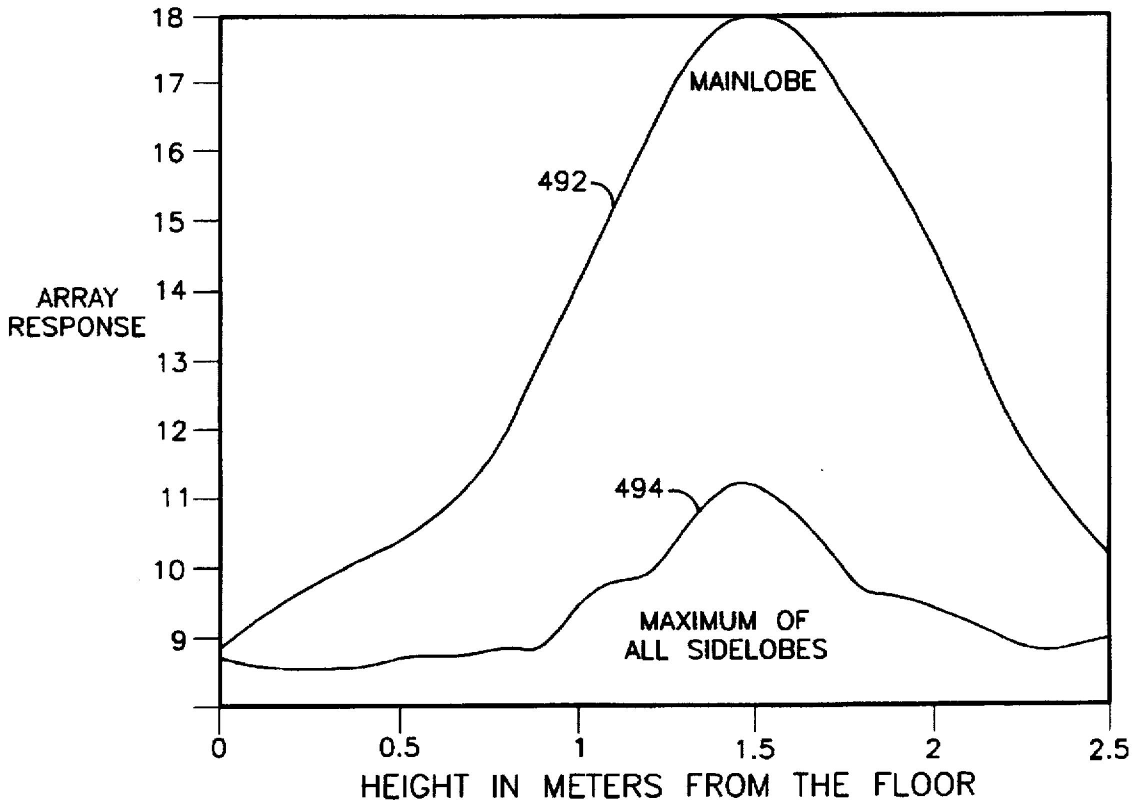
FIG. 14 is a graph of acoustic response of three sensor-arrays showing main lobe and side-lobes from floor to ceiling, in accordance with the present invention.
Figure 15:
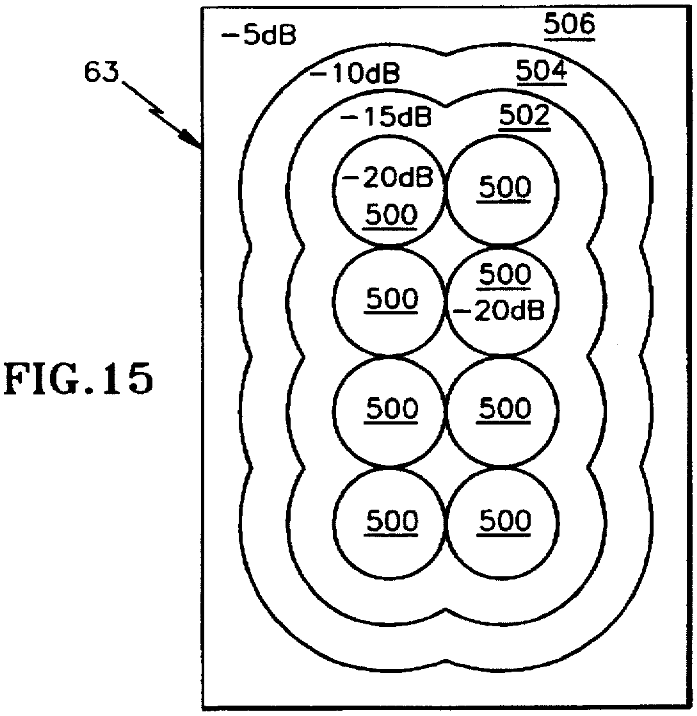
FIG. 15 is a diagram showing multiple quiet regions and the amount of noise attenuation at such regions, in accordance with the present invention.

Referring now to FIGS. 13–15, for the room 63 described in FIG. 10, if the three arrays 50,77,400 are focused to intersect at the region 410 (at a location of 1.5 meters from the floor in the x-y plane), the peak (or main lobe) microphone response is at a point 490 at the volume 410, substantially at the center of the room 63 and a lower response is exhibited at side lobes 491. The vertical axis of FIG. 13 is scaled for the maximum response of one (1.0) from each sensor, giving a total maximum response of 18.

In that case, for a noise frequency of 450 hertz, the weighting factors W1–W18 have the values: W1=1.9088; W2=2.0121; W3=1.2108; W4=1.5039; W5=0.8642; W6=0.3779; W7=0.0394; W8=1.0668;W9=0.5822; W10=1.5100; W11=–0.2569; W12=1.2502; W13=0.2681; W14=1.0047; w15=1.4878; w16=0.8470; w17=0.9244; W18=1.3987; and the delays D1–D18 have the values: D1=0.00000000λ, D2=0.30200475λ, D3=0.47851537λ, D4=0.47851537λ, D5=0.30200475λ, D6=0.00000000λ, D7=0.48486530λ, D8=0.71125886λ, D9=0.83417616λ, D10=0.83417616λ, D11=0.71125886λ, D12=0.48486530λ, D13=0.97581922λ, D14=0.22063103λ, D15=0.38561872λ, D16=0.45392830λ, D17=0.41725348λ, D18=0.28016212λ. Delays D1–D12 are the same as shown for the two arrays of FIG. 4. Delays D13–D18 are not symmetric because, while the array is centered vertically, the focus beam is at 1.5 meters and the room has a height (H) of 2.5 meters. Also, the microphones in the arrays 50,77,400 are equally spaced apart at λ/2. The microphones may be spaced closer if desired, but, if they are all equally spaced, they should not be spaced much farther apart than λ/2 to avoid spatial aliasing, as discussed hereinbefore. The spacing between the arrays 50,77,400 is determined by the size of the room 63 and of the walls 65,67. Other microphone spacings may be used as discussed hereinafter.

The eighteen weighting factors W1–W18 and delays D1–D18 were optimized simultaneously to provide maximum (main lobe) response at the center of the room and low side lobe response (at least 2:1 reduction from the main lobe) outside the center of the room using near field analysis and constrained optimization software in MATLAB® as discussed hereinbefore. Alternatively, if a far field analysis was performed, all the delays D1–D18 would be 1 for focusing the main beams at the center of the room 63.

Referring to FIG. 14, because three dimensions and three arrays are used, other regions of the cab above and below this plane will be substantially quiet near the floor and near the ceiling of the room 63, respectively. In particular, a curve 492 indicates the array response for the main lobe, i.e., along the line 306 from the floor to the ceiling, and a curve 494 indicates the maximum side lobe response at points outside the line 306 from floor to ceiling.

Referring now to FIG. 15, a plurality of regions 500 around the room 63 may be simultaneously detected and quieted by using the three phased-array microphones 77,50,400 over a region of space near the ears of the occupants in the room 63. The active noise control logic 20 can maximize the quietness at the regions 500 providing, e.g., –20 db, of attenuation in these regions. Accordingly, in regions 502, 504,506 outside the quiet zone 500, less attenuation will be exhibited, e.g., −15, −10, −5 dB, respectively. Thus, the invention allows for quieting a plurality of selective regions remote from where the microphones are located. Other amounts of attenuation and/or attenuation patterns may be used if desired.

Instead of quieting eight regions as indicated in FIG. 15, many more regions may be quieted if desired for any of the embodiments discussed herein. In that case, the number of quieted regions (or volumes) may be greater than the number of microphones used, which, for the embodiment of FIG. 10, was eighteen.

Further, the microphones in a given array need not be evenly spaced relative to each other, i.e., irregular spacing may be used if desired, thereby creating a "thinned" or "sparse" array, i.e., having microphone spacing which is not the same for each adjacent pair of microphones. Such a thinned array may have at least one pair of mics spaced less than or equal to λ/2, where λ corresponds to the highest frequency the system must detect and cancel; however, this constraint is not required in a thinned array, as is known. Thinned arrays are discussed more fully in numerous sources including: D. H. Johnson, et al, "Array Signal Processing: Concepts and Techniques", Prentice Hall, Englewood Cliffs, N.J. (1993), Ch. 3, Section 2, entitled "Spatial Sampling", and Section 3 entitled "Arrays of Discrete Sensors", pp. 77–106. Thinning is specifically discussed on page 101 in Section 3.3.5 entitled "Sparse Linear Arrays".

Also, one or more of the microphone arrays may be a two dimensional array if desired. Further, each sensor array need not be in the form of a linear sensor array (i.e., the sensors in a given array need not be positioned along a straight line).

Figure 16:
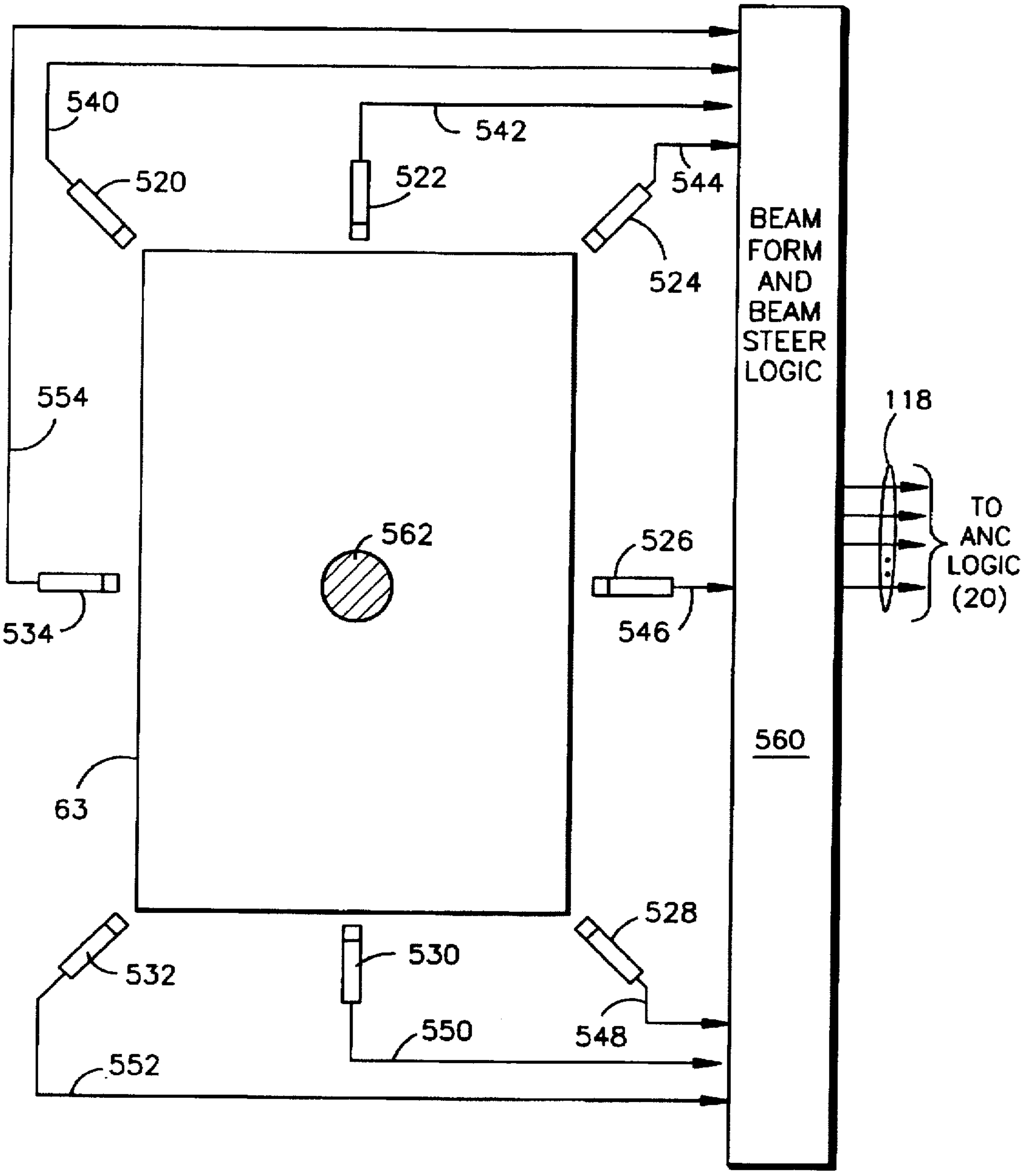
FIG. 16 is a top view of a room and a block diagram of an active noise control system employing a distributed phased-array of sensors, in accordance with the present invention.
Figure 17:
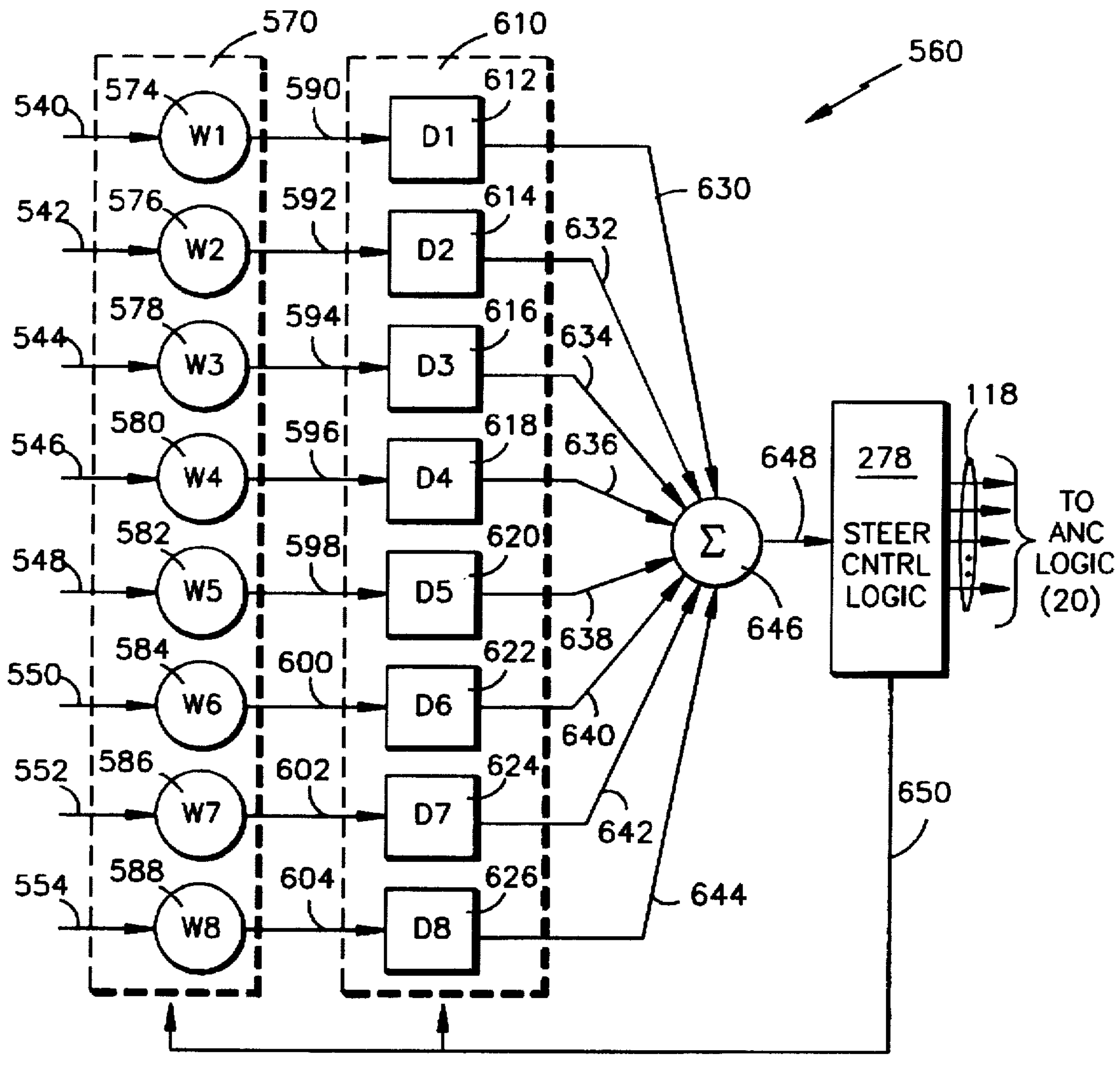
FIG. 17 is a block diagram of beam forming and beam steering logic for a the system of FIG. 16, in accordance with the present invention.

Referring to FIGS. 16 and 17, alternatively, the error sensors need not be in the form of a plurality of sensor arrays, but may be distributed at predetermined locations throughout the room. In that case, the weighting factors Wn would be chosen such that the acoustic response of the entire group of sensors provides a quieted volume at the desired location. In particular, referring to FIG. 16, eight microphones 520–534 (mics) are distributed around the perimeter of the room 63 and provide electrical signals on lines 540–554 to beam form and beam steer logic 560 similar to the logics 76 (FIG. 3) and 416 (FIG. 11) discussed hereinbefore. The logic 560 is designed to tailor the acoustic response of all the microphones 520–534 so as to have maximum acoustic response at a selectable predetermined volume 562 as discussed hereinafter. The spacing of the distributed mics 520–534 may likely be non-uniform (e.g., a thinned distribution) around the perimeter of the room especially if any of the spacings between some or all of the microphones is more than λ/2. If the mics.520–534 are located all at the same height (z), the acoustic response will, in general, provide a vertical column as discussed hereinbefore with the two arrays 50,77 (FIG. 2). However, if the mics 520–534 are placed not all at the same height(z), a smaller z-axis focus is obtained, thereby allowing for a smaller quiet volume (along the z-axis). Alternatively, a z-array (not shown), such as the array 400 (FIG. 10) oriented along the z-axis may be used to provide smaller z-axis fucussing, and, accordingly, a smaller quiet volume along the z-axis. In general, the more mics that are used, the better the spatial resolution and the smaller the quiet regions may be.

Referring to FIG. 17, the beam form and beam steer logic 560 comprises beam form logic 570 comprising eight multipliers 574–588 which multiply the signals on the lines 540–554 by weighting factors W1–W8, respectively. The beam form logic 560 provides eight weighted output signals on lines 590–604 from the multipliers 574–588, respectively, to beam steer logic 610. The beam steer logic 610 comprises eight variable delays 612–626 (D1–D8). The variable delays D1–D8 delay the signals on the lines 590–604 by a predetermined amount unique for each microphone in the distributed array. By adjusting the delay on the signals from each of the microphones, the peak acoustic response for the array may be tuned so as to sense noise from different regions of the room in the same fashion as discussed hereinbefore. The beam steer logic 610 provides weighted delayed signals on lines 630–644 for each of the microphones 520–534, respectively. The weighted delayed signals are fed to a summer 646 which sums the signals on the lines 630–644 and provides a slummed output signal for the distributed array on a line 648.

The signal on the line 648 is fed to the steer control logic 278 discussed hereinbefore, which provides signals on lines 650 to the beam steer logic 610 to adjust the delays D1–D12 which adjust the peak acoustic response of the distributed array to different regions around the room. In certain cases, the weighting factors W1–W8 may also need to be adjusted by the steer control logic 278 to retain optimized acoustic response at the desired location. This may likely be necessary when near field analysis is performed to determine the weighting factors Wn as discussed hereinbefore. A sequential signal from each of the regions to be quieted is coupled from the line 648 to an associated one of the lines 118 by the logic 278 which are fed to the active noise control logic 20, as discussed hereinbefore. The values of the weights W1–W8 and the delays D1–D8 are selected using the same techniques as that discussed hereinbefore for selecting and optimizing weights and delays (i.e., FLATLAB®), where all the microphones are optimized as a group, or using other techniques as discussed hereinafter.

It should be understood that instead of performing the beam steering logic 100, 236, 330, 610 (FIGS. 3,9,12,17, respectively) sequentially, it may be performed simultaneously by routing the input signals to the delays to a plurality of different delays simultaneously and then summing them together. In that case, the steer control logic 278 would not be needed and the output signal for each location to be quieted would all be fed simultaneously to the control logic 20 on an associated one of the lines 118. A similar simultaneous configuration applies to the beam forming logics 150,210,428,570 (FIGS. 3,9,12,17, respectively) if it is also variable.

Also, it should be understood that the beam forming and beam steering logics described herein may be achieved using any of the known beam forming and beam steering techniques described in the prior art, such as those described in the articles: Flanagan et al., "Computer-Steered Microphone Arrays For Sound Transduction In Large Rooms", Journal of Acoustical Society of America, Vol. 78, No. 5 (November 1985); Flanagan et al., "Autodirective Microphone Systems", Acoustica, Vol. 73 (1991); or Takahashi et al., "Self-adapting Multiple Microphone System", Sensors and Actuators, pages 610–614, 1990; or in U.S. Pat. No. 4,829,590, entitled "Adaptive Noise Abatement System", to Ghose. Still further, any mathematical technique for determining the noise in a volume of space at a physical location remote from the sensors may be used if desired.

Further, other optimization software and/or techniques than those discussed herein may be used if desired. Also, other ratios of main lobe to side lobe response may be used if desired; however, in general, the main lobe width (or size of the volume to be sensed and quieted) is inversely proportional to the side lobe height. Thus, the larger the volume to be sensed and quieted, the smaller the side lobe peaks will be.

Also, it should be understood that the sense microphones 10 need not be employed. In that case, no feed-forward logic would be utilized in the active noise control logic 20 and the system would be purely a feedback system utilizing the phased-array microphones as the feedback control sensors.

Further, the sequence of the delays and weighting factors may be reversed if desired. Also, in general, the weighting factors Wn and/or delays Dn may be implemented by multiplication by one or more complex numbers having a magnitude and phase associated therewith.

Although the invention has been described and illustrated with respect to the exemplary embodiments thereof, it should be understood by those skilled in the art that the foregoing and various other changes, omissions and additions may be made without departing from the spirit and scope of the invention.

We claim:

1. An active noise control system, comprising:

sensor means for detecting noise waves and for providing noise signals indicative of said waves;

beam means for receiving said noise signals, for causing said sensor means to have an acoustic response profile which is selectively responsive to solely a predetermined quiet region remote from said sensor means, and for providing a beam signal indicative of noise at said quiet region; and noise control means responsive to said beam signal for providing an anti-noise signal which substantially cancels said noise at said quiet region.

2. The noise control system of claim 1 wherein said sensing means comprises a plurality of sensor arrays.

3. The noise control system of claim 2 wherein at least one of said sensor arrays comprises a thinned array.

4. The noise control system of claim 2 wherein at least one of said sensor arrays comprises a linear array.

5. The noise control system of claim 2 wherein said acoustic response profile comprises a plurality of individual acoustic response profiles, one corresponding to each of said sensor arrays, and said quiet region comprises the intersection of said individual response profiles.

6. The noise control system of claim 1 wherein said sensing means comprises a plurality of distributed sensors.

7. The noise control system of claim 6 wherein at least two of said sensors are spaced apart no more than one half of the wavelength of the highest frequency of said noise waves to be canceled.

8. The noise control system of claim 1 further comprising feedforward sensing means for sensing said noise waves and for providing a feedforward noise signal to said noise control means.

9. The noise control system of claim 1 wherein said noise control means comprises at least one speaker for providing said anti-noise signal.

10. The noise control system of claim 1 wherein said noise control means comprises Filtered-X control logic.

11. The noise control system of claim 1 wherein said noise control means comprises Filtered-U control logic.

* * * * *